United States Patent [19]

Banko

[11] Patent Number: 4,496,342

[45] Date of Patent: Jan. 29, 1985

[54] SURGE PREVENTION SYSTEM FOR AN OPHTHALMIC INSTRUMENT

[75] Inventor: Anton Banko, Bronx, N.Y.

[73] Assignee: Surgical Design Corporation, Long Island City, N.Y.

[21] Appl. No.: 245,664

[22] Filed: Mar. 20, 1981

[51] Int. Cl.³ .............................................. A61M 1/00
[52] U.S. Cl. ...................................... 604/27; 604/31; 604/22
[58] Field of Search ............... 128/683, 276, 305, 760, 128/24 A, 214 E; 417/26, 38, 476; 434/59; 604/27, 28, 30, 31

[56] References Cited

U.S. PATENT DOCUMENTS

| | | | |
|---|---|---|---|
| 2,988,001 | 6/1961 | D'Arcey et al. | 417/476 |
| 3,572,319 | 3/1971 | Bittner et al. | 604/31 |
| 3,905,353 | 9/1975 | Lichowsky | 128/683 |
| 3,920,014 | 11/1975 | Banko | 128/276 |
| 4,024,866 | 5/1977 | Wallach | 128/276 |
| 4,168,707 | 9/1979 | Douvas et al. | 128/276 |
| 4,324,243 | 4/1982 | Helfgott | 128/276 |

Primary Examiner—C. Fred Rosenbaum
Assistant Examiner—J. L. Kruter
Attorney, Agent, or Firm—Darby & Darby

[57] ABSTRACT

An instrument for removing liquid and other material from an operating site through an evacuation line under the control of a pump, in which the fluid flow in the line is sensed and a control signal produced when material blocking the line is cleared thereby creating a surge in the fluid flow coming into the line, wherein the control signal operates to apply fluid from a separate source into the line and to stop the pump motor to thereby rapidly equalize the pressure between the operating site and the line. An arrangement is also provided to sense evacuation flow in the line when the pump is not operating and to apply the fluid from the separate source into the line to equalize the pressure.

8 Claims, 2 Drawing Figures

SURGE PREVENTION SYSTEM FOR AN OPHTHALMIC INSTRUMENT

During microsurgery in a closed environment, for example intraocular surgery in the eye, a requirement exists for material to be evacuated through an instrument. The material, which is generally a mixture of a liquid and solid tissue, the mixture hereafter called a fluid, has either been cut or emulsified or removed by some other process from a portion of the operating site. At the same time, an infusion fluid such as a saline solution, is placed into the operating site to replace the removed fluid so that the operating site will stay physically formed or at a given pressure. The exchange rate of the fluid has to be kept at a predetermined level to facilitate removal of the severed tissue to thereby maintain the operating site in a "frozen" condition such that the material to be removed does not move around.

In particular, in operating in the eye, a small intraocular pressure above atmospheric, for example up to about 40 mmHg is desired during surgery. The diameter of the instrument through which the severed tissue is removed is kept small so that the incision into the eye can also be made as small as possible. The same holds true with respect to the infusion instrument which can, for example, be a part of the evacuating instrument. The small intraocular pressure and the small possible differential pressure limits the infusion rate.

On the other hand, it is desired that the evacuation rate be kept constant. Arrangements for doing this and for controlling other flow conditions are shown in my U.S. Pat. Nos. 3,812,855 granted May 28, 1974; 3,920,014 granted Nov. 18, 1975; 4,007,742 granted Feb. 15, 1977; 4,019,514 granted Apr. 26, 1977; and 4,117,843 granted Oct. 3, 1978, all of which are assigned to the same assignee. The evacuation rate will stay constant as long as there are no particles which will occlude the evacuation passage of the instrument performing the evacuation. The evacuation process can cause a reduction and fluctuation in intraocular pressure. If the infusion fluid is furnished by gravity feed, for example from an intravenous fluid bottle hung at a predetermined distance above the operating site, the evacuating flow rate must not exceed the infusion flow rate to keep the intraocular pressure constant and to prevent eye collapse. A constant evacuation rate has to be maintained where the infusion rate is constant in order to keep a constant intraocular pressure.

When the evacuation passage of the instrument is occluded, the evacuation flow rate is reduced due to higher resistance to motion in the evacuation line. Blockage of the evacuation line, assuming that the infusion fluid is still being supplied, results in a buildup in the intraocular pressure.

If the occlusion is at or near the entrance port of the evacuation instrument and is suddenly removed, there will be a sudden surge of the fluid into the evacuation orifice. This causes a surge of fluid from the eye thereby causing a sudden drop in the intraocular pressure. This results in a turbulence within the eye, the turbulence being particularly noted at the evacuation port of the instrument. Usually some sort of a cutting or emulsification mechanism is located at or adjacent to the inlet port of the evacuation instrument. After a period of time, the surge will smooth out and the eye will reach an equilibrium pressure.

The present invention is directed to an arrangement for reducing the surge of energy brought about by the sudden removal of a blockage from the evacuation instrument. In accordance with the invention, an instrument is provided having an arrangement wherein a surge prevention fluid flow is provided into the instrument evacuation passage when the instrument senses that the passage was blocked and then suddenly becomes unblocked. This flow acts ge to counteract the sudden surge of fluid into the evacuation line.

It is therefore an object of the present invention to provide a surge protection system for a surgical instrument.

A further object is to provide a surge protection system for a surgical instrument in which the flow rate, or pressure, in the evacuation line is being sensed and when there is a sudden increase, a line is opened to restore fluid to the evacuation line between the instrument and the evacuation pump.

Other objects and advantages of the present invention will become more apparent upon reference to the following specification and annexed drawings in which.

Figure 1:
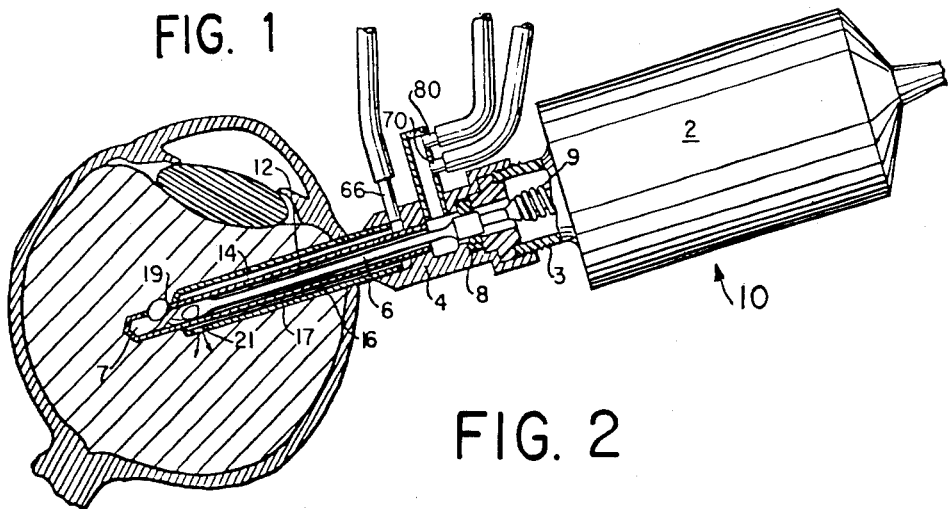
FIG. 1 is an overall plan view, taken partly in cross-section, of a typical instrument for use with a system of the present invention.

FIG. 1 shows a typical surgical instrument 10 with which the system can be used. It should be understood, however, that the system can be used with any type of instrument or instrument set-up which requires infusion flow of a fluid and/or evacuation of fluid and severed material from an operating site. This includes any of a number of various types of mechanical cutting instruments (e.g. choppers, rotating cutters, guillotine type cutters, etc.) as well as other instruments, for example those of the ultrasonic type, which emulsify material to be removed.

In the embodiment of the invention being described, the tip of instrument 10 is shown as having pierced through a section of the eye, for example after an incision has been made. The tip of the instrument is shown in the vitreous of the eye to remove tissue therefrom or to treat the eye. The instrument of FIG. 1 also can be used to remove material from other parts of the eye such as the lens or iris. It should be understood that the system can be used with any compatible type of instrument to perform operations or treatment in any portion of the body of a mammal.

The instrument 10 of FIG. 1 includes an electric motor 2, preferably of the reversible type, from which extends a collar 3. A fitting 4 is fastened onto collar 3 and concentric inner and outer tubular members 12 and 16 extend from fitting 4. Inner tube 12 defines a central passage 14 through which evacuation takes place over a line 70, to be described below, which communicates with passage 14 through a coupling on fitting 4. The space between the inner and the outer tubes 12 and 16 defines a passage 17 through which infusion fluid is supplied over a line 66.

The inner, evacuation flow, member 14 of the instrument has an opening 19 at the end thereof through which the evacuation flow communicates with the operation field. The infusion flow member 16 has an opening 21 in its wall, spaced from opening 19 to avoid interference, through which fluid is injected into the operating field.

A shaft 6, illustratively shown as having a fluid cutter 7 at the end thereof is located in the inner passage 14. The shaft is connected to the motor 2 and rotates in bearings 8 in the fitting 4. Shaft 6 is preferably biased by a spring 9 so that the cutter 7 will coact with the surface surrounding the evacuation opening 19 to produce a shearing action to cut any tissue therebetween. In operation, the tip of the instrument is moved to place the cutter 7 at the site of the material to be severed. The evacuation flow from opening 19 aids in drawing the material into a relationship so that it can be severed by cutter 7. The severed material, in suspension or as part of an emulsion, is drawn up passage 14 and is removed via passage 14.

At the time the evacuation is taking place, infusion fluid is supplied over line 66 to the eye through passage 17 and its opening 21. This is to keep the intraocular pressure as constant as possible.

Figure 2:
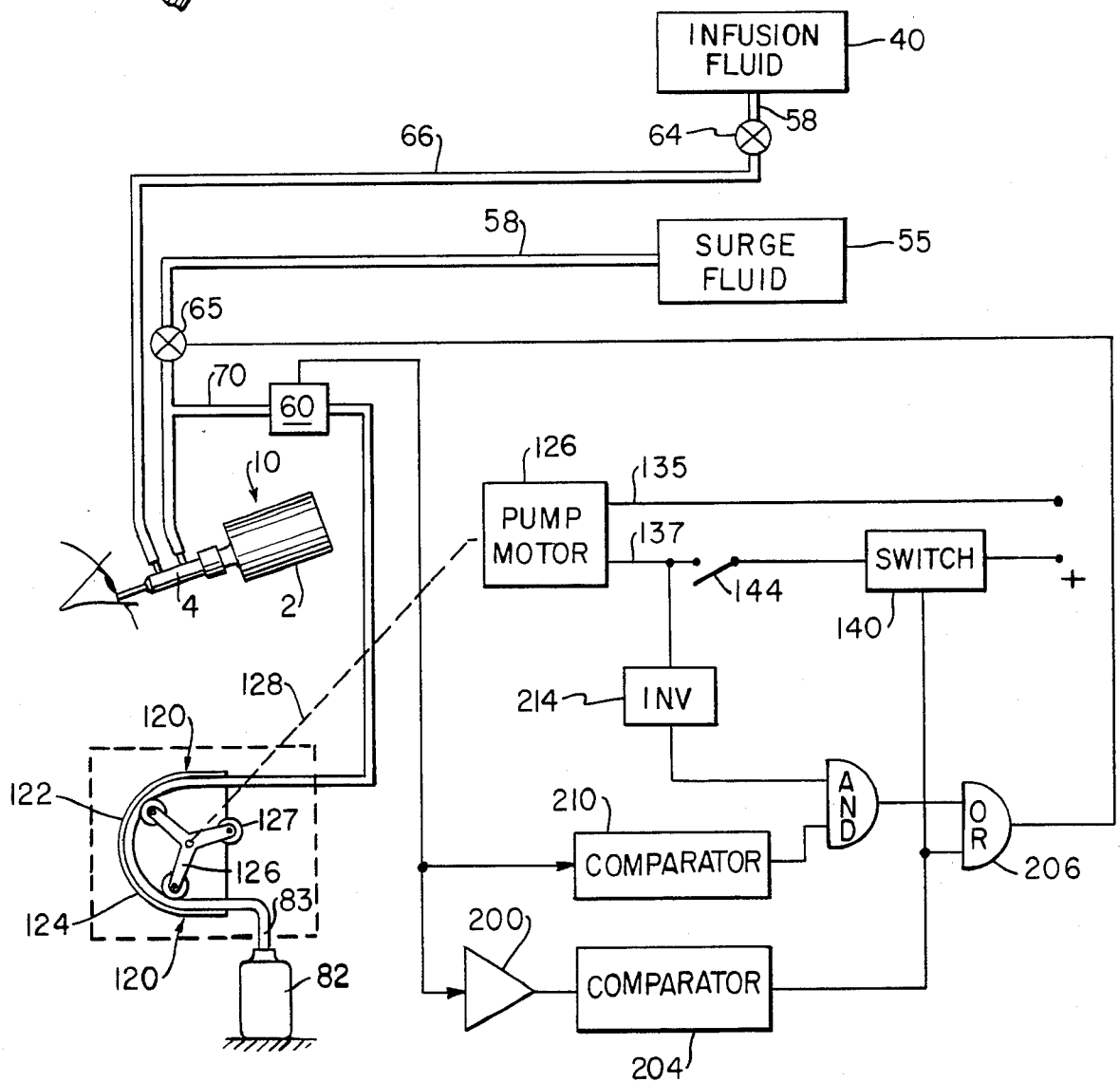
FIG. 2 is a schematic line diagram showing the various components of the system and their operation with particular emphasis on the fluid flow portions of the system and their various components.

Referring to FIG. 2, a portion of the instrument is shown with respect to the outflow line 70 and the infusion line 66. The infusion fluid is shown in a bottle 40 and is a control valve 64 of the electromechanical type preferably provided in the line 66. Valve 64 is not critical to the operation of the subject invention so it is not described further. There is also shown a source of surge fluid 55 which can be a bottle or a bag which preferably is located at a higher position relative to the source of infusion fluid 40 so that it will have a higher pressure.

A flow transducer 60 is located in the evacuation line 70 which proceeds to a pump 120. Pump 120 is preferably of the peristaltic type and includes a rotor 126 having three equally spaced rollers 127 mounted thereon which is driven by a motor 125. The instrument evacuation line 70 is connected to a compressible tubing at the entrance to a housing 122 of generally semi-circular shape. The tubing A has an outlet 83 to a waste bottle 82.

As the rotor 126 rotates, the fluid ahead of the roller 127 engaging the tubing pushes fluid out of the pump and additional fluid is drawn into the pump. The principles of operation of the pump 120 are well known.

The source of surge fluid 55 is connected via a line 58 and an electromechanically controlled valve 65 to the output side of the transducer 60 between the evacuation line 70 and the pump 120. The transducer produces an output voltage control signal in proportion to the rate of fluid flow therethrough.

The pump 120 is driven by a pump motor 125, which can be of either the AC or DC type, although a DC motor is illustratively shown, and the output shaft 128 for the pump is shown. The pump motor 125 has an input voltage control shown by a negative, or common, supply line 135 and a positive supply line 137. The positive side 137 has a suitable switch 140 therein which can be of the electromechanical (e.g., a relay) or electronic type (e.g., a transistor). Also in series in the positive line 135 is a mechanically or electromechanically operated switch 144 which can be for example, on the operating foot pedal or other similar circuit for the instrument. The switch 144 would also be connected, for example, to whatever operating portions of the system such as the motor for the handpiece, the ultrasonic generator if an ultrasonic instrument is to be used, etc.

The output of the transducer 60 is applied to an electronic circuit for sensing the various operating conditions of the system and, particularly, conditions in the evacuation line 70. The output voltage signal from the transducer is proportional to the flow rate in the evacuation line 70. It is applied to a differentiating amplifier 200 whose output is connected to a comparator circuit 204. The output of the comparator 204 in turn is applied to one input of an OR circuit 206 and also to an electronic or electromechanically controlled switch 140 in the positive side supply line 135 of the pump 126.

Considering the surge condition which was referred to above, when the evacuation line 70 is blocked, for example by there being occluding material at the evacuation port 19 of the instrument, the pump 120 would normally keep operating. This causes emptying out the evacuation line 70 between the tip of the instrument and the pump. The amount that the line empties depends upon the length of time that the blockage occurs. To understand the operation of the system, consider that switch 144 is closed during normal operation of the instrument and the pump motor 126 is operating. The blockage of the line will cause a decrease in the flow rate measured by transducer 60. This will cause a changing voltage output of the transducer 60. This change in the flow rate will generally be gradual since the fluid flow rate decreases gradually as the line 70 empties out. As the fluid empties out of line 70, the negative (suction) pressure builds up since the pump is still running.

When the blockage is removed, the negative pressure built up in the line 70 tends to draw material out from the eye quite rapidly to fill up the empty line 70. When this occurs, the transducer 60 will produce a rapidly increasing voltage corresponding to the sudden increase in flow rate in line 70.

The differentiator circuit 200 is constructed to sense this positively, rapidly increasing voltage. Any suitable conventional circuit can be used, for example, an operational amplifier wired as a differentiator. The time constant of the differentiating amplifer is selected so that it will not produce an output signal when the evacuation flow is steady or is decreasing at a gradual rate. The output of the differentiating amplifier 200 is applied to the comparator 204 which will produce an output signal when the differentiating amplifier 200 produces a signal corresponding to a rate of change of the output signal from the transducer 60 which corresponds to the sudden release of the blocking material. That is, the combination of the differentiating amplifier 200 and the comparator 204 will sense the release of the material blocking the evacuation line.

To reduce or minimize the inflow surge at the tip of the instrument, the output signal from the comparator 204 performs two functions. The first function is controlled through OR circuit 206 to open the valve 65 in the surge fluid line 58. When valve 65 is opened, fluid is immediately dumped into the evacuation line 70 filling up the empty space in the line between the instrument and the pump and, also, in some measure, creating somewhat of a back flow in the line 70 to the instrument evacuation port. This has the effect of equalizing the pressure between the eye and the line so that there is no surge of fluid from the eye into the evacuation line.

The second function is for the output signal of the comparator 204 to produce a signal which will open the switch 140 to shut off the motor. Thus, not only is the surge fluid supplied to the line 70 but at the same time the evacuation pump 120 is stopped. This arrangement will equalize the pressure in the eye very rapidly thereby reducing the surge.

In the operation of the system, another condition encountered is one wherein the switch 144 is closed, pump 120 is stopped and there is a negative (suction) pressure in the evacuation line 70 but no tissue removal is being accomplished. In this case the negative pressure in the line 80 will tend to gradually remove the fluid and material from the operating site. This condition is not readily discernible, but it is desirable to eliminate it to provide a more optimum stabilization of the field.

To accomplish this, the output signal from the transducer 60 is also supplied to a comparator 210 which produces an output signal corresponding to a negative pressure in line 70 above a predetermined value. It should be understood that pressure and flow rate in line 70 are related. The output of the comparator circuit is applied to an AND gate 212 whose other input is from the positive supply line 137 to the pump motor through an inverter 214. Thus, if the switch 144 is open, meaning that no voltage is supplied to the pump motor to cause it to operate, and there is a negative suction on the line 70 above a predetermined level, the AND gate 212 will receive two input signals causing it to produce an output. The output from the AND gate 212 is applied through the OR circuit 206 to the valve 65 to cause the valve 65 to open. This will apply fluid from the surge fluid supply 55 into the evacuation line 80 thereby effectively placing the evacuation line 70 at a zero, or equilibrium pressure with respect to the operating site.

What is claimed is:

1. A material removal system for an opthalmic instrument comprising:

instrument means having an evacuation port for placement into an operating site and a flow line communicating with said evacuation port of said instrument means for evacuating material from said site, pump means communicating with said flow line for creating a liquid fluid flow through said flow line, means for sensing the rate of fluid flow in said flow line, a source of liquid, means for admitting liquid from said source into said flow line at a point between the evacuation port of said instrument and said pump means, means including comparator means coupled to said sensing means for producing a signal corresponding to a rapid rate change going from a low fluid flow rate condition such that if the flow line were clogged to a high fluid flow rate condition in said flow line above a predetermined level, and means responsive to said signal for operating said liquid admitting means to supply the liquid from said source into said flow line to aid in filling the empty volume in said line and to tend to equalize the pressure in said line between the operating site and said pump means and for stopping the operation of said pump means.

2. A system as in claim 1 wherein said instrument means includes tubular means defining a passage communicating with said flow line through which the evacuation flow takes place and an opening in the tubular means defining said evacuation port, the blockage of said port or passage causing a reduction in the fluid flow rate in said flow line sensed by said sensing means and the unblocking causing an increase in the fluid flow rate.

3. A system as in claim 2 wherein said means for producing said signal comprises circuit means for sensing the rate of change of flow and for producing said signal when the rate of change exceeds a predetermined level.

4. A system as in claim 3 wherein said circuit means comprises differentiator circuit means coupled to the output of said sensor means, and signal level detecting means coupled to said differentiator circuit means.

5. A system as in claim 1 wherein said pump means comprises a peristaltic pump.

6. A system as in claim 1 further comprising means coupled to said sensing means and said pump means for producing a second signal to operate said admitting means to supply the liquid from said source into said flow line when said pump is inoperative and fluid is flowing in said line at a rate above a predetermined rate.

7. A system as in claim 6 wherein said means for producing said second signal comprises means for detecting a flow rate above a given rate.

8. A material removal system for opthalmic instrument comprising:

said instrument having an evacuation port for placement into an operating site and an evacuation flow line communicating with said port for evacuating material from said site, pump means communicating with said evacuation flow line for creating an evacuation fluid flow through said flow line and said instrument to said operating site, means for sensing the rate of fluid flow in said evacuation flow line, a source of liquid, means for admitting liquid from said source into said evacuation flow line at a point between said instrument and said pump, means including comparator means coupled to said sensing means for producing a first signal corresponding to a change from a first rate of flow to a second and higher rate of flow at or above a predetermined rate, and means coupled to said first signal producing means and said pump responsive to said signal to operate said admitting means to supply the liquid from said source to said evacuation flow line when said pump is inoperative and fluid is flowing in said line at a rate above a given predetermined rate.

* * * * *